United States Patent [19]

Schmid et al.

[11] Patent Number: 4,889,925
[45] Date of Patent: Dec. 26, 1989

[54] PROCESS FOR THE PURIFICATION OF ALKYL GLYCOSIDES, PRODUCTS OBTAINABLE BY THIS PROCESS AND THEIR USE

[75] Inventors: Karl H. Schmid, Mettmann; Manfred Biermann, Muehlheim, both of Fed. Rep. of Germany

[73] Assignee: Henkel Kommanditgesellschaft auf Aktien, Duesseldorf, Fed. Rep. of Germany

[21] Appl. No.: 10,864

[22] Filed: Feb. 4, 1987

[30] Foreign Application Priority Data

Feb. 6, 1986 [DE]  Fed. Rep. of Germany ....... 3603581

[51] Int. Cl.$^4$ .................. C07H 15/04; C07H 1/06; A61K 7/00; C11D 1/66
[52] U.S. Cl. .................. 536/18.6; 514/844; 514/846; 536/4.1; 536/18.5; 536/124; 536/127
[58] Field of Search ............. 536/4.1, 18.5, 18.6, 536/124, 127; 514/844, 846

[56] References Cited

U.S. PATENT DOCUMENTS

| | | | |
|---|---|---|---|
| 3,598,865 | 8/1971 | Lew | 536/4.1 |
| 3,772,269 | 11/1973 | Lew | 536/4.1 |
| 3,839,318 | 10/1974 | Mansfield | 536/18.6 |
| 4,349,669 | 9/1982 | Klahr et al. | 536/127 |
| 4,393,203 | 7/1983 | Mao et al. | 536/124 |
| 4,483,979 | 11/1984 | Mao | 536/4.1 |
| 4,488,981 | 12/1984 | Urfer et al. | 536/18.6 |
| 4,510,306 | 4/1985 | Langdon | 536/18.6 |

Primary Examiner—Ronald W. Griffin
Attorney, Agent, or Firm—Ernie G. Szoke; Wayne C. Jaeschke; Real J. Grandmaison

[57] ABSTRACT

Mixtures of alkyl glycosides and fatty alcohols are readily separated by distillation without thermal degradation of glycoside. In the presence of one or more viscosity-reducing agents which are heat-stable and color-stable at temperatures of up to 160° C., which are miscible with the alkyl glycosides, which have a boiling point at 760 mbar at least 50° C. above the boiling point of the fatty alcohol present in the mixture, and reduce the viscosity of the mixture to at most 10,000 mPas at the distillation temperature. The fatty alcohols are quantitatively separated off from this mixture by distillation in customary distillation apparatus at a temperature at least 20° C. below the thermal decomposition point of the alky glycosides and under pressures of from 1 to $10^{-3}$ bar. The process is particularly applicable to the purification of reaction mixtures obtained from the preparation of alkyl glycosides from fatty alcohols and saccharides to provide a product comprising alkyl glycoside and viscosity-reducing agent directly useable is cosmetics and fabric detergents, dishwashing detergents and cleaning preparations.

23 Claims, No Drawings

PROCESS FOR THE PURIFICATION OF ALKYL GLYCOSIDES, PRODUCTS OBTAINABLE BY THIS PROCESS AND THEIR USE

BACKGROUND OF THE INVENTION

1. Field of the Invention

This invention relates to a process for the purification of alkyl glycosides by distillation, to the mixtures obtained as the products of this distillation process, and to compositions containing the mixtures.

2. Statement of Related Art

Alkyl glycosides are formed by the reaction of monosaccharides with fatty alcohols. The alkyl glycoside products can be used for a variety of purposes, for example, as detergents, wetting agents, gelling agents, lubricants, food emulsifiers, and the like.

The production of lower alkyl monoglycosides by the Fischer process, in which a monosaccharide and a fatty alcohol containing up to 10 carbon atoms in the alkyl group are reacted with one another in the presence of an acidic catalyst, has been known for some time. Such alkyl glycosides are widely used as surfactants. The reaction of the two components with one another is highly selective and the hydrophilicity of the alkyl glycosides obtained is adjustable by varying the molar ratio of fatty alcohol to monosaccharide. Products containing two or more monosaccharide units exhibit higher solubility in water than alkyl monoglycosides.

Processes for the production of higher alkyl monoglycosides and alkyl ollgoglycosides and mixtures thereof, in which the alkyl group contains from 8 to 25 carbon atoms, are also known, for example from U.S. Pat. Nos. 3,722,269; 3,598,865 and 3,839,318. However, the processes described in these publications have several disadvantages so far as industrial syntheses are concerned. The monosaccharides and fatty alcohols employed have only limited miscibility with one another, necessitating the presence of a suitable solvent compatible with both components which has to be separated off in the following step and returned to the process. In addition, oligomers and colored compounds are formed to an often undesirable degree during the reaction and have to be removed at a later stage by elaborate separation procedures. Also, the hydrophilicity of the alkyl glycosides obtained cannot be controlled via the number of monosaccharide units in the molecule.

However, the main disadvantage of state-of-the-art processes is that they can only provide alkyl glycoside/-fatty alcohol mixtures in which the ratio of alkyl glycoside to fatty alcohol is from 1:10 to 2:1. Accordingly, the removal of unreacted fatty alcohol from the alkyl glycosides before their practical application is unavoidable, and both solvent extraction and distillation procedures are employed.

According to U.S. Pat. No. 3,839,318, excess fatty alcohol is separated from the glycoside/fatty alcohol reaction mixture by a technically very involved method requiring the use of an additional solvent which must in turn be separated off in an additional process step and, in the interests of economy, must be recovered and returned to the process. Accordingly, this process cannot be carried out in one step. It is therefore preferable to purify crude product alkyl glycosides by distilling off excess fatty alcohol; unfortunately, this is technically difficult because the product alkyl glycosides typically have melting points above 70° C. The melting point of the alkyl glycosides increases with increasing degree of glycosidation, and the viscosity of the products is very high in the vicinity of their melting temperature. Alkyl monoglycosides are only fluid, stirrable, and pumpable above 120° C., while alkyl ollgoglycosides are solids even at higher temperatures. Where thin-layer evaporators are used for the distillation process, as described for example, in U.S. Pat. No. 4,393,203, these viscosity problems are particularly acute: highly viscous contituents of the unpurified reaction mixture solidify in the thin-layer evaporator. Further, most alkyl glycosides show only limited thermal stability. The decomposition reaction begins significantly at temperatures as low as 130° C., resulting in undesirable darkening of the products and in the formation of sugar alcohols. Especially with thin-film reactors, dark-colored degradation products or so-called "sugar charcoal" are soon formed, resulting in a distinct reduction in the quality of the desired products. For these reasons, the process for purifying alkyl glycosides described in U.S. Pat. No. 4,393,203 is limited in its application and can only be applied where the products obtained do not have to meet stringent quality requirements.

U.S. Pat. No. 4,349,669 describes a process for the purification of alkyl glycosides containing from 8 to 16 carbon atoms in the alkyl group by distillation of unreacted fatty alcohols in which the last remnants of fatty alcohol are separated from the product by distillation in the presence of glycols having boiling points higher than those of alcohols to be separated by at most 10° C. and lower by at most 30° C. By addition of the glycol, residues of fatty alcohols are entrained from the product mixture, and also, the product alkyl glycosides are present in dilute and hence low-viscosity form for the duration of the distillation process. The disadvantage of this process from the point of view of industrial manufacturing is that, once again, an entraining agent or solvent, namely a glycol again, an entraining agent or solvent, namely a glycol or a mixture of several glycols, has to be added to the reaction mixture, necessitating an additional step for recovering and recycling this "auxiliary".

DESCRIPTION OF THE INVENTION

Other than in the operating examples, or where otherwise indicated, all numbers expressing quantities of ingredients or reaction conditions used herein are to be understood as modified in all instances by the term "about".

The present invention provides a distillation process for the production of purified alkyl glycosides which obviates the use of distillation auxiliaries, and thus eliminates the necessity for their consequent removal and reintroduction into the manufacturing process by elaborate process steps. More particularly, the invention provides a distillation process for the preparation of a purified alkyl glycoside composition substantially free from fatty alcohol residues, which exhibits surface-active properties and which is directly usable in cosmetics, in fabric and dishwashing detergents, and in other cleaning preparations. Residual fatty alcohol product content of below about 5% by weight is typical.

According to the process, crude alkyl glycoside reaction mixtures containing alkyl glycosides and unreacted fatty alcohol residues are distilled in the presence of viscosity-reducing polar organic compounds to remove fatty alcohol residues. Surprisingly, the viscosity-reducing agents according to the invention not only afford a distinct reduction in viscosity and consequently better handling characteristics of the reaction mixture, but also depress the melting point of the alkyl glycosides, so that the purification of these reaction mixtures by distillation results in less thermal stress on these derivatives. As a result, substantially fatty-alcohol-free, high quality alkyl glycosides, which are easy to handle on a large scale by virtue of their low viscosity, are obtainable at distillation temperatures substantially below the thermal decomposition point of the alkyl glycosides. The product alkyl glycosides are eminently suitable as surfactants in a variety of applications because the solubility of the glycosides in water is also improved.

Accordingly, the present invention comprises a process for the separation of alkyl glycosides and fatty alcohols by distillation of mixtures containing both components, wherein at least one polar organic viscosity-reducing agent which (a) is heat-stable and color-stable at a temperature of up to 160° C.;
(b) is miscible with the alkyl glycosides in the mixture;
(c) has a boiling point at 760 mbar of at least 50° C. above the boiling point of the fatty alcohol present in the mixture; and
(d) reduces the viscosity of the mixture to at most 10,000 mPas at the distillation temperature, typically from about 120° C. up to 160° C., in a quantity of from 10 to 50%, particularly from 20 to 50%, by weight of the mixture, is added to the mixture, and the fatty alcohols present are quantitatively separated off by distillation from the low-viscosity mixtures in conventional distillation apparatus at a temperature at least 20° C. below the thermal decomposition point of the alkyl glycosides and under a pressure of from 1 to $10^{-3}$ bar. Preferably, the viscosity-reducing agent also functions to substantially depress the melting point of the alkyl glycoside to at least below about 100° C. for most applications. Typically, the mixture to be purified according to the process of the invention is a reaction mixture comprising products of the reaction of a fatty alcohol and a mono- or oligo-saccharide, or mixtures thereof, to form a crude product comprising corresponding alkyl glycosides and unreacted fatty alcohol. Purification of mixtures containing excess alcohol having a carbon atom content of up to at least 25 carbon atoms and, typically, at least 8 carbon atoms, is especially contemplated. The viscosity of the reaction mixtures to be distilled is important to the process according to the invention; typically, the mixtures are not pumpable under distillation conditions without addition of the viscosity-reducing agents according to the invention. (The term "pumpable" is used herein to characterize solutions or liquid reaction mixtures which have a viscosity of no more than 10,000 mPas at the distillation temperature.)

The present invention further comprises compositions containing alkyl glycosides in a quantity of from 90 to 50% by weight and one or more viscosity-reducing agents which are heat-stable and color-stable at a temperature of up to 160° C., and which are miscible with the alkyl glycosides, which have a boiling point at 760 mbar at least 50° C. above the boiling point of the fatty alcohol component of the alkyl glycosides, and which function to reduce the viscosity of corresponding alkyl glycoside/fatty alcohol mixtures containing a weight ratio of alkyl glycoside to fatty alcohol of from 1:10 to 2:1, to at most 10,000 mPas at a temperature of from 120° C. up to 160° C. in a quantity of from 10 to 50%, preferably from 20 to 50%, by weight of the mixture.

In addition, the present invention comprises detergent and cosmetic compositions, especially fabric detergents, dishwashing detergents, and cleaning compositions for domestic and industrial applications, which include alkyl glycoside/viscosity-reducing agent compositions, preferably as directly obtained according to the process of the invention. Viscosity-reducing agents which potentiate the practical performance of the alkyl glycosides such products, for example by acting as detergents, wetting agents, emulsifiers, foam inhibitors or detergency boosters in support of the alkyl glycosides, are particularly preferred; the agents are employable either individually or as mixtures.

Preferably, one or more of the following compounds are selected for use in the process according to the invention:

(a) vicinal diols and vicinal hydroxyamines derived from the epoxides of olefins, unsaturated fatty acids, or unsaturated fatty alcohols containing from 8 to 22 carbon atoms in the carbon chain;
(b) adducts of ethylene oxide, propylene oxide, butylene oxide, or mixtures thereof with fatty derivatives of the formula:

$$Y-R^1-X$$

in which
X is COOH, OH, NR$^2$H or CONH$_2$:
Y is H, OH or CH(OH)R$^3$;
R$^1$ is unbranched or branched C$_8$–C$_{22}$-alkylene or -alkenylene;
R$^2$ is H, unbranched or branched C$_1$–C$_8$-alkyl, or (CH$_2$)$_m$NH$_2$ wherein m is 2 or 3; and
R$^3$ is H, or unbranched or branched C$_1$–C$_6$-alkyl;

(c) adducts of ethylene oxide and/or propylene oxide with a linear or cyclic hydroxy compound containing from 1 to 6 hydroxy groups and from 1 to 6 carbon atoms, or polyglycerol; and
(d) ether derivatives of the formula:

$$A-O-R^4$$

in which
A is the residue of a compound of one of the described groups (a), (b), or (c) after removal of a hydrogen atom; and
R$^4$ is unbranched or branched C$_1$–C$_8$-alkyl or -alkenyl; CH$_2$OR$^5$, wherein R$^5$ is unbranched or branched C$_1$–C$_{18}$-alkyl; R$^6$COOH, wherein R$^6$ is methylene, ethylene or trimethylene; and NR$^7_2$, wherein R$^7$ is H, C$_1$–C$_4$-alkyl, or hydroxy-C$_1$–C$_4$-alkylene.

Fatty alkyl etheramines, and, in particular, ethoxylates thereof, are very suitable.

In a particularly preferred embodiment of the invention, a fatty alcohol ethoxylate containing from 12 to 18 carbon atoms in the alkyl group of the alcohol and from 3 to 10 moles ethylene oxide per mole fatty alcohol are used in the process of the invention as viscosity-reducing agents for the separation of alkyl glycosides and fatty alcohols. Fatty alcohol ethoxylates containing from 12 to 14 carbon atoms in the alkyl group of the alcohol and 5 moles ethylene oxide per mole fatty alcohol are especially preferred. These fatty alcohol ethoxylates may be used either individually or in admixture with one another. Exemplary fatty alcohol ethoxylates suitable for use in accordance with the invention are compounds of the formula:

$$C_mH_{2m+1}O(CH_2CH_2O)_nH$$

in which
m is an integer of from 12 to 18, preferably from 12 to 14; and
n is an integer of from 3 to 10, preferably 5; and in which ($C_mH_{2m+1}$) is unsubstituted or is substituted, especially hydroxy-substituted, preferably with less than 6 hydroxy radicals.

It is of particular advantage to use fatty alcohol ethoxylates derived from mixtures of fatty alcohols, especially alcohols comprising adducts of cocosalcohol with 5 moles ethylene oxide, cocosalcohol with 3 moles ethylene oxide, tallow alcohol with 5 moles ethylene oxide and oxo alcohol with 7 moles ethylene oxide. "Cocosalcohol" is defined herein as a mixture of fatty alcohols of synthetic or natural origin each containing from 12 to 18 carbon atoms and "cocosamine" is the corresponding mixture of fatty amines; "tallow alcohol" is defined herein as a mixture of fatty alcohols of synthetic or natural origin each containing from 16 to 18 carbon atoms; and "oxo alcohol" is defined herein as a mixture of fatty alcohols from an oxo synthesis each containing from 14 to 15 carbon atoms. An adduct of 3,5-dihydroxy-1-pentadecanol with 10 moles ethylene oxide is especially representative of fatty alcohol ethoxylates corresponding to the above formula, in which the alkyl group ($C_mH_{2m+1}$) contains hydroxyl substituents.

In another preferred embodiment, 1,2-alkane diols containing from 12 to 18 carbon atoms and preferably from 12 to 14 carbon atoms in the alkyl group are used as viscosity-reducing agents instead of the described fatty alcohol ethoxylates. The alkane diols are used individually or as mixtures of two or more in any desired ratio. The 1,2-alkane diols correspond to the formula:

$$HOCH_2—CH(OH)—C_pH_{2p+1}$$

in which p is an integer of from 10 to 16, preferably of from 10 to 12.

According to the invention, suitable diols include, for example, 1,2dodecanediol, 1,2-tridecanediol, 1,2-tetradecanediol, 1,2-pentadecanediol, 1,2-hexadeca-nediol, 1,2-heptadecanediol, 1,2-octadecanediol, or mixtures thereof. Both the straight-chain and branched-chain isomers of the 1,2-diols are useful, although the straight-chain isomers are generally preferably used because of their ready availability from natural sources. Within this group, 1,2-dodecanediol, 1,2-tridecanediol and 1,2-tetradecanediol are particularly useful, especially 1,2-dodecanediol.

In another embodiment, adducts of ethylene oxide and/or propylene oxide with fatty alcohols, fatty amines and fatty acids corresponding to the above formula Y—$R^1$—X, in which X, Y and $R^1$ are as defined above, and either derivatives of compounds corresponding to the above formula A—O—$R^4$, in which A and $R^4$ are as defined above, are added as viscosity-reducing agents. Such compounds include, for example, adducts of cocosamine with 4 moles ethylene oxide, cocosamine with 12 moles ethylene oxide, adducts of cocosalcohol with 5 moles ethylene oxide and 4 moles propylene oxide or with 4 moles ethylene oxide and 5 moles propylene oxide, adducts of technical oleic acid with 5.5 moles ethylene oxide and also 10-(diethanolamino)-1-octadecanol. Suitable ether derivatives include compounds corresponding to the above formula A—O—$R^4$, in which A is the residue of an adduct of cocosalcohol with 9 moles ethylene oxide after removal of a hydrogen atom and $R^4$ is alkyl containing from 1 to 4 carbon atoms, preferably 4 carbon atoms; and also ether derivatives corresponding to the same formula in which A is the residue of an adduct of cocosalcohol with 1 to 10 moles, preferably 4 to 5 moles, ethylene oxide; and $R^4$ is $NR_2^7$, in which $R^7$ is as defined above.

The reaction mixtures containing the above-mentioned viscosity-reducing agents are distilled in conventional distillation apparatus, typically comprising a standard apparatus suitable for sump-phase distillation or for other non-continuous distillation processes, or thin-layer evaporators or comparable apparatus known and used in art-related continuous distillation processes. In order to achieve quantitative separation of the unreacted fatty alcohols from the reaction mixture by distillation, the distillation process is generally carried out under normal pressure. In order to further reduce the distillation temperature of the process according to the invention, distillation may also be carried out under reduced pressure, for example from below 1 down to $10^{-3}$ bar. Such reduced pressures may be required in the purification of mixtures containing higher (8 to 25 carbon atoms) fatty alcohols to permit quantitative separation of the alcohols without thermal degradation of the alkyl glycosides. Typically, pressures above about $10^{-2}$ bar are adequate.

The additives according to the invention function to reduce the viscosity of the mixtures containing alkyl glycosides and fatty alcohols. They have particular advantage over other viscosity-reducing agents in that, in addition to reducing the viscosity of the crude alkyl glycoside reaction product, they also surprisingly lower the melting point of the alkyl glycosides, so that the distillation process for the separation of excess fatty alcohols is effective at a temperature distinctly below the thermal decomposition point of the alkyl glycoside component. Preferably, a distillation temperature at least 20° C. below the thermal decomposition point of the glycoside component is employed.

Because of the low distillation temperatures made possible by the additives according to the invention, reaction mixtures do not become discolored owing to degradation of the easily thermally-decomposed alkyl glycosides. There is no need whatever in the process according to the invention for the customary bleaching step generally required in known processes, in which reaction products containing alkyl glycosides are bleached with hydrogen peroxide solution to ensure that the end product meets stringent quality requirements. Additionally, the alkyl glycoside purification product has improved solubility in water.

Thus, the process according to the invention provides product compositions which contain alkyl glycosides in a quantity of from 90 to 50% by weight in combination with one or more viscosity-reducing agents. These compositions require no further after-treatment and are characterized by a high-grade alkyl glycoside component of good color and improved solubility in water. Preferably, these compositions include one or more viscosity-reducing agents in a quantity of from 10 to 50% by weight, desirably selected to enhance the desired performance properties of the alkyl glycosides, for example to improve their effectiveness as detergents, wetting agents, emulsifiers, foam inhibitors or detergency boosters. One or more viscosity-reducing agents selected from among the following compounds are advantageously combined with alkyl glycosides according to the invention in an amount of from 10 to 50% by weight to improve the properties thereof and provide compositions for use in a variety of applications:

(a) vicinal diols and vicinal hydroxyamines derived from the epoxides of olefins, unsaturated fatty acids, or unsaturated fatty alcohols containing from 8 to 22 carbon atoms in the carbon chain;

(b) adducts of ethylene oxide propylene oxide, or butylene oxide, or mixtures thereof with fatty derivatives of the formula:

$$Y-R^1-X$$

in which

X is COOH, OH, $NR^2H$, or $CONH_2$;
Y is H, OH, or $CH(OH)R^3$;
$R^1$ is unbranched or branched $C_8-C_{22}$-alkylene or -alkenylene;
$R^2$ is H, unbranched or branched $C_1-C_8$-alkyl, or $(CH_2)_mNH_2$ wherein m is 2 or 3; and $R^3$ is H or unbranched or branched $C_1-C_6$-alkyl;

(c) adducts of ethylene oxide or propylene oxide or mixtures thereof with linear or cyclic hydroxy compounds containing from 1 to 6 hydroxy groups and from 1 to 6 carbon atoms, or with polyglycerol: and (d) ether derivatives of the formula $$A-O-R^4$$

in which

A is the residue of a compound within the scope of the above mentioned groups (a), (b), or (c), after removal of a hydrogen atom; and
$R^4$ is unbranched or branched $C_1-C_{18}$-alkyl or -alkenyl; $CH_2OR^5$ wherein $R^5$ is unbranched or branched $C_1-C_{18}$-alkyl; $R^6COOH$, wherein $R^6$ is methylene, ethylene or trimethylene; or $NR^7_2$, wherein $R^7$ is hydrogen, $C_1-C_4$-alkyl, or $C_1-C_4$-hydroxyalkylene.

In particularly preferred embodiments, the compositions contain one or more fatty alcohol ethoxylates having the structures set forth supra, or, alternatively, one or more alkane diols as set forth supra, in a quantity of from 10 to 50% by weight, preferably 20 to 50% by weight, as the viscosity reducing agents. By virtue of their particularly broad range of application, compositions containing the purified alkyl glycosides and fatty alcohol ethoxylates or 1,2-alkane diols in a weight ratio of from 80:20 to 50:50 are preferred.

For particular applications, for example in the production of hair shampoos, it is often desirable to make up alkyl glycosides in the form of 70 to 80% aqueous solutions. The easiest way of doing this is to directly mix the purified liquid alkyl glycoside melt with water. In the process according to the invention, the melting point of the alkyl glycoside mixtures is preferably depressed to below 100° C. by the viscosity-reducing additives present, especially fatty alcohol ethoxylate or 1,2-alkane diol additives, which also considerably improve the solubility of the products in water. As a result, the mixtures are readily incorporated in water in the absence of the applied pressure which is otherwise frequently necessary in practice. In the latter case, compositions containing alkyl glycosides in a quantity of from 75 to 40% by weight; a viscosity-reducing agent comprising a fatty alcohol ethoxylate or a 1,2-alkane diol in a quantity of from 5 to 40% by weight; and water in a quantity of from 20 to 30% by weight; are obtained as preferred compositions.

Compositions according to the invention are useful in various applications. They exhibit excellent miscibility with water and are used either individually or, if desired, in admixture with other surfactants for the production of cosmetics, and also in fabric detergents, dishwashing detergents, and cleaning preparations for domestic and industrial applications.

The invention is illustrated by the following Examples.

EXAMPLE 1

A reaction mixture from the production of dodecyl-tetradecyl monoglucoside still contained 81% by weight of the fatty alcohol mixture from the production process (direct synthesis: reaction of dodecanol/tetradecanol with glucose in the presence of sulfuric acid as catalyst to form the monoglucoside). The pure monoglucoside is solid at 80° C. and has a viscosity of 3695 Pa.s at 130° C.

A fatty alcohol ethoxylate containing from 12 to 14 carbon atoms in the alkyl group of the alcohol and having an average content of 5 moles ethylene oxide per mole fatty alcohol was added to the reaction mixture. Liquefaction (reduction in viscosity) was achieved with the mixing ratios shown in Table 1 below which also shows the viscosity values.

TABLE 1

| Alkyl glycoside | Addition[a] | Viscosity/aggregrate state at | |
|---|---|---|---|
| (% by weight) | (% by weight) | 80° C. (Pa.s) | 130° C. (Pa.s) |
| a | 100 | 0 | —/solid | 3,695/liquid |
| b | 80 | 20 | 1.420/stirrable paste | 91/liquid |
| c | 50 | 50 | 60/liquid | 12/liquid |

[a] adduct of dodecanol/tetradecanol (70:30) with 5EO

EXAMPLE 2

In the same way as in Example 1, a mixture of 1,2-dodecanediol and 1,2-tetradecanediol in the amounts indicated in Table 2 below was added to reaction mixtures from the production of dodecyl/tetradecyl monoglucoside. The viscosities of the compositions obtained and their aggregate state are also shown in Table 2.

TABLE 2

| Alkyl glycoside | Addition[b] | Viscosity/aggregrate state at | |
|---|---|---|---|
| (% by weight) | (% by weight) | 80° C. (Pa.s) | 130° C. (Pa.s) |
| a | 100 | 0 | —/solid | 3.695/liquid |
| b | 80 | 20 | 4.045/liquid | 139/still pumpable |
| c | 50 | 50 | 199/liquid | 20/liquid |

[b] 1,2-dodecanediol/1,2-tetradecanediol (70:30)

EXAMPLE 3

An adduct of dodecanol/tetradecanol with 5EO was added in the quantities indicated in Table 3 to a reaction mixture from the direct synthesis of dodecyl/tetradecyl ollgoglucoside (average degree of glucosidation 2.2) from the corresponding fatty alcohol mixture and glucose in the presence of sulfuric acid as catalyst which still contained 65% by weight of the fatty alcohol from the synthesis. The reaction mixture without any viscosity-reducing additive was solid at 80° C. and viscous in consistency at 130° C.; addition of the fatty alcohol ethoxylate in the quantities indicated in Table 3 produced a distinct reduction in viscosity.

TABLE 3

| | Alkyl glycoside | Addition[a] | Viscosity/aggregate state at | |
|---|---|---|---|---|
| | (% by weight) | (% by weight) | 80° C. (Pa.s) | 130° C. (Pa.s) |
| a | 100 | 0 | —/solid | 24.650/viscous |
| b | 80 | 20 | 47.200/stirrable paste | 1 130/liquid |
| c | 50 | 50 | 181/liquid | 46/liquid |

[a]adduct of dodecanol/tetradecanol (70:30) with 5 EO

EXAMPLE 4

A mixture of 1,2-dodecanediol and 1,2-tetradecanediol was added to the reaction mixture described in Example 3 in the amounts shown in Table 4. A distinct reduction in viscosity was also obtained by addition of the diol mixture. The viscosity values are shown in Table 4 below.

TABLE 4

| | Alkyl glycoside | Addition[b] | Viscosity/aggregrate state at | |
|---|---|---|---|---|
| | (% by weight) | (% by weight) | 80° C. (Pa.s) | 130° C. (Pa.s) |
| a | 100 | 0 | —/solid | 24.650/viscous |
| b | 80 | 20 | —/liquid | 1.835/still pumpable |
| c | 50 | 50 | 610/liquid | 68/liquid |

[b]1,2-dodecanediol/1,2-tetradecanediol (70:30)

EXAMPLE 5

The reaction mixtures described in Examples 1 to 4 were subjected to continuous distillation in a thin-layer evaporator. The thin-layer evaporator had the following parameters:

| | |
|---|---|
| area of the heating jacket | 500 cm$^2$ |
| rotational speed | 285 min$^{-1}$ |
| peripheral speed | 76 cm.s$^{-1}$ |

The described reaction mixtures were introduced through a dropping funnel heated with steam to approximately 60°–80° C. The cold finger of the thin-layer evaporator was operated with cold or hot water according to the melting point of the fatty alcohol. Distillate and residue were collected in separate receiving flasks. Where necessary, the outlet pipe of the thin-layer evaporator was additionally heated by radiation to melt any fractions of substance which did not flow down smoothly.

The operating parameters and also the residual content of fatty alcohol in the mixture after the first distillation cycle are shown in Table 5.

In the continuous distillation of the reaction mixtures described in Examples 1 to 4, it was found that not only were the batches which did not contain any viscosity-reducing additives considerably more difficult to handle even at room temperatures, they were also difficult to distill, even at elevated temperature. Fractions of alkyl glucoside were repeatedly observed to solidify in the outlet pipe of the thin-layer evaporator. In addition, the residual content of fatty alcohol after a distillation cycle was very high.

By contrast, the reaction mixtures described in Examples 1-4 containing the viscosity-reducing additives could be distilled without difficulty in the thin-layer evaporator. No fractions of alkyl glucoside were seen to solidify or stop. The reaction mixtures ran down in a coherent film. The residual fatty alcohol content could be reduced to a very low value in only the first distillation cycle.

COMPARISON EXAMPLE 1

A reaction mixture from the direct synthesis of dodecyl monoglucoside which still contained 81% by weight of unreacted dodecanol was distilled in a thin-layer evaporator without the addition of a viscosity-reducing agent according to the invention. The process parameters are shown in Table 5. For a through-put of 120 ml of the reaction mixture per minute, it was found that poorly soluble fractions of the reaction mixture solidified in the thin-layer evaporator and only ran down after melting, and the distillate still had a residual dodecanol content of 11% after one distillation cycle.

COMPARISON EXAMPLE 2

A reaction mixture from the direct synthesis of dodecyl monoglucoside, which still contained 81% by weight of unreacted dodecanol, was subjected to thin-layer distillation under the conditions shown in Table 5 without the addition of a viscosity-reducing agent. In this case, too, unmelted parts of the reaction mixture were seen to solidify and had to be removed from the thin-layer evaporator by melting. After one distillation cycle, the residual dodecanol content was less than 1%.

TABLE 5

| Mixture of Example | Temp. of heating jacket (°C.) | Pressure (mbar) | Throughout (ml/min.) | Residual content ROH (wt. %) |
|---|---|---|---|---|
| 1b | 100 | $10^{-2}$ | 170 | 5.8 |
| C1 | 100 | $10^{-2}$ | 120 | 11.0 |
| C2 | 150 | $10^{-1}$ | 180 | <1 |

We claim:
1. A method for purifying an alkyl glycoside/fatty alcohol mixture by distillation compromising:
   (a) adding to the mixture at least one polar organic viscosity-reducing agent, miscible with the alkyl glycoside, which is color-stable and heat-stable at the distillation temperature and which has a boiling point at least about 50° C. above the boiling point of the fatty alcohol component at 760 mbar, in an amount sufficient to reduce the viscosity of the mixture to a viscosity of no more than 20,000 mPas under distillation conditions, selected from a group consisting of (1) fatty alcohol ethoxylates containing from 12 to 18 carbon atoms in the fatty alcohol moiety and from 3 to 10 mols of ethylene oxide per mol of fatty alcohol, and (2) 1,2-alkane diols containing from 12 to 18 carbon atoms; and
   (b) quantitatively distilling off fatty alcohol from the alkyl glycoside/fatty alcohol mixture at a temperature of up to about 160° C. and at least about 20° C. below the thermal decomposition point of the alkyl glycoside component, and under a pressure of from about 1 to $10^{-3}$ to substantially eliminate fatty alcohol from the mixture and provide a mixture, with reduced fatty alcohol content, comprising alkyl glycoside and from 10 to 50% by weight of the mixture, with reduced fatty alcohol content, of the at least one polar organic viscosity reducing agent.

2. The process of claim 1, wherein the mixture is a reaction mixture containing products of the reaction of a fatty alcohol and a saccharide to form an alkyl glycoside.

3. The process of claim 2, wherein the viscosity-reducing agent is added in an amount from about 10 to 50% by weight of the mixture.

4. The process of claim 2, wherein the viscosity-reducing agent depresses the melting point of the mixture to below about 100° C.

5. The process of claim 2, wherein the viscosity-reducing agent further functions to potentiate the properties of the alkyl glycoside component of the mixture.

6. The process of claim 2, wherein the viscosity-reducing agent functions as a detergent, wetting agent, emulsifier, foam inhibitor or detergency booster.

7. The process of claim 1, wherein from about 10 to 50% by weight of the fatty alcohol ethoxylate or 1,2-alkane diol is added to the mixture.

8. The process of claim 1, wherein an adduct comprising a fatty alcohol ethoxylate containing from 12 to 14 carbon atoms in the alkyl moiety of the alcohol and 5 moles ethylene oxide per mole fatty alcohol is added.

9. The process of claim 1, wherein a 1,2-alkane diol or a mixture of 1,2-alkane diols containing from 12 to 14 carbon atoms is used.

10. A composition comprising:
(a) an alkyl glycoside in a quantity of from about 90 to 50% by weight of the composition; and
(b) at least one viscosity-reducing polar organic agent in an amount of from about 10 to 50% by weight of the composition which is heat-stable and color-stable at a temperature of up to about 160° C., which is miscible with the alkyl glycoside, which has a boiling point at 760 mbar of at least 50° C. above the boiling point of the fatty alcohol component of the alkyl glycoside, and which functions in said amount to decrease the viscosity of a mixture consisting essentially of said alkyl glycoside and said fatty alcohol in a weight ratio of from about 1:10 to 2:1 to at most about 10,000 mPas at a temperature of from about 120° C. up to about 160° C., wherein the viscosity-reducing agent is selected from the group consisting of
(1) fatty alcohol ethoxylates containing from 12 to 18 carbon atoms in the fatty alcohol moiety and from 3 to 10 moles ethylene oxide per mole of fatty alcohol, and
(2) 1,2-alkane diols containing from 12 to 18 carbon atoms.

11. The composition of claim 10, wherein the viscosity-reducing agent is present in an amount of from about 20 to 50% by weight of the composition.

12. The composition of claim 11, wherein the viscosity-reducing agent functions as a detergent, wetting agent, emulsifier, foam inhibitor or detergency booster.

13. The composition of claim 11, wherein the fatty alcohol ethoxylate or 1,2-alkane diol is present in a ratio by weight of the alkylglycoside to viscosity-reducing agent of from about 80:20 to 50:50.

14. The composition of claim 11, wherein
(a) the alkyl glycoside is present in a quantity of from about 75 to 40% by weight of the composition;
(b) the fatty alcohol ethoxylate or 1,2-alkane diol is present in an amount of from about 5 to 40% by weight of the composition;
and wherein the composition further includes water in an amount of from about 20 to 30% by weight of the composition.

15. In a cosmetic, cleaning, or detergent composition including an alkyl glycoside, the improvement comprising substituting the viscosity-reduced alkyl glycoside composition of claim 10 for the alkyl glycoside.

16. In a cosmetic, cleaning, or detergent composition including an alkyl glycoside, the improvement comprising substituting the viscosity-reduced alkyl glycoside composition of claim 11 for the alkyl glycoside.

17. The purified reaction mixture obtained according to the purification process of claim 3.

18. A detergent, cleaning, or cosmetic composition containing the purified reaction mixture of claim 17.

19. The purified reaction mixture of claim 17, wherein the mixture contains from about 20 to 50% by weight of the viscosity-reducing agent.

20. The purified reaction mixture of claim 19, further including water in an amount of from about 20 to 30% by weight of the mixture.

21. The purified reaction mixture of claim 17, wherein a $C_{12}$–$C_{14}$-1,2-alkane diol or an ethoxylate of a $C_{12}$–$C_{14}$-fatty alcohol is added.

22. The purified reaction mixture of claim 21, wherein an ethoxylate of a $C_{12}$–$C_{14}$-fatty alcohol with 5 moles ethylene oxide per mole alcohol is added.

23. The purified reaction mixture of claim 17, wherein from about 20 to 50% of the viscosity-reducing agent is added.

* * * * *